United States Patent
Armand et al.

(10) Patent No.: US 10,869,639 B2
(45) Date of Patent: Dec. 22, 2020

(54) METHOD AND SYSTEM FOR DETERMINING A TRAJECTORY OF AN X-RAY IMAGING SYSTEM

(71) Applicant: SURGIVISIO, Gieres (FR)

(72) Inventors: David Armand, Saint Egreve (FR); Arnaud Pierre, La Tronche (FR); Laurence Van Beek, Saint Martin d'Uriage (FR); Stephane Lavallee, Saint Martin d'Uriage (FR)

(73) Assignee: SURGIVISIO, Gieres (FR)

( * ) Notice: Subject to any disclaimer, the term of this patent is extended or adjusted under 35 U.S.C. 154(b) by 0 days.

(21) Appl. No.: 16/345,187

(22) PCT Filed: Oct. 26, 2017

(86) PCT No.: PCT/EP2017/077446
§ 371 (c)(1),
(2) Date: Apr. 25, 2019

(87) PCT Pub. No.: WO2018/078017
PCT Pub. Date: May 3, 2018

(65) Prior Publication Data
US 2019/0282183 A1   Sep. 19, 2019

(30) Foreign Application Priority Data

Oct. 28, 2016   (EP) .................................. 16306422

(51) Int. Cl.
*A61B 6/00* (2006.01)
*A61B 6/02* (2006.01)
(Continued)

(52) U.S. Cl.
CPC .............. *A61B 6/027* (2013.01); *A61B 6/025* (2013.01); *A61B 6/032* (2013.01); *A61B 6/4441* (2013.01);
(Continued)

(58) Field of Classification Search
CPC .. A61B 2017/00712; A61B 2034/2059; A61B 2090/367; A61B 2090/376;
(Continued)

(56) References Cited

U.S. PATENT DOCUMENTS 6,715,918 B2 * 4/2004 Mitschke ............... A61B 6/583
378/163
7,016,456 B2 * 3/2006 Basu ...................... A61B 6/032
378/18
(Continued)

OTHER PUBLICATIONS

European Search Report and Written Opinion received for EP Patent Application No. 163064223, completed on Apr. 24, 2017, 4 pages.
(Continued)

*Primary Examiner* — Irakli Kiknadze
(74) *Attorney, Agent, or Firm* — Womble Bond Dickinson (US) LLP (57) ABSTRACT

The invention relates to a method for determining a trajectory of a motorized X-ray imaging system for acquiring images of a patient to whom a phantom comprising radiopaque fiducials having a known spatial arrangement has been attached so as to be visible on at least one 2D image of a body region of interest acquired by the X-ray imaging system by acquiring one first 2D image of the phantom by the X-ray imaging system in a given position; detecting the fiducials of the phantom in the acquired first image; based on the detected fiducials, determining the position of the phantom in a referential of the X-ray imaging system; determining a set of positions of the X-ray imaging system configured to acquire a set of 2D X-ray images of the region of interest such that the set of 2D X-ray images complies with at least one imposed requirement on the position of the phantom relative to a part of the set of images and combining the set
(Continued)

of determined positions to determine a trajectory of the X-ray imaging system with respect to the position of the phantom.

15 Claims, 4 Drawing Sheets

(51) Int. Cl.
*A61B 90/00* (2016.01)
*A61B 6/03* (2006.01)
*A61B 34/20* (2016.01)
*A61B 17/00* (2006.01)

(52) U.S. Cl.
CPC .......... *A61B 6/4476* (2013.01); *A61B 6/505* (2013.01); *A61B 6/545* (2013.01); *A61B 6/583* (2013.01); *A61B 6/584* (2013.01); *A61B 90/36* (2016.02); *A61B 6/469* (2013.01); *A61B 2017/00712* (2013.01); *A61B 2034/2059* (2016.02); *A61B 2090/367* (2016.02); *A61B 2090/376* (2016.02); *A61B 2090/3966* (2016.02)

(58) Field of Classification Search
CPC . A61B 2090/3966; A61B 6/025; A61B 6/027; A61B 6/032; A61B 6/4441; A61B 6/4476; A61B 6/469; A61B 6/545; A61B 6/586; A61B 5/1075; A61B 6/04; A61B 6/06; A61B 6/08; A61B 6/4014; A61B 6/463; A61B 6/505; A61B 6/588; A61B 6/0407; A61B 6/4405; A61B 6/5205; A61B 6/535; A61B 6/584; A61B 34/20; A61B 6/12; A61B 6/583; A61B 2090/392; A61B 6/5247; A61B 90/36; A61B 2090/3937; A61B 90/39; A61B 2034/2048; A61B 2017/00725; A61B 2034/2051; A61B 5/06; A61B 6/487; A61B 6/582; G06T 11/006; G06T 2207/10116; G06T 2207/20048; G06T 2211/424; G06T 2207/30204; G06T 2207/10081; G06T 7/33; G06T 7/80; G06T 2207/30004; G06T 2207/10088; G06T 2207/10121; G06T 2207/10136; G06T 2207/20; G06T 2207/20221; G06T 2211/436; G06T 11/005; G06K 9/2054; G06K 9/2063; G06K 9/6203; G06K 9/78; G06K 9/80; G01R 33/4808; G01R 33/4812; G01R 33/58; G01N 2223/1006; G01N 2223/401; G01N 2223/419; G01N 23/04; G01N 23/046; G01N 2223/303
USPC .................................. 378/4, 19, 62, 207, 18
See application file for complete search history.

(56) References Cited

U.S. PATENT DOCUMENTS

| 2010/0177948 | A1 | 7/2010 | Le Bras |
| 2015/0003577 | A1 | 1/2015 | Aulbach et al. |
| 2015/0125033 | A1* | 5/2015 | Murphy .................. G06T 7/251 |
| | | | 382/103 |
| 2016/0242724 | A1 | 8/2016 | Lavallee et al. |

OTHER PUBLICATIONS

International Preliminary Report on Patentability received for PCT Patent Application No. PCT/EP2017/077446, dated May 9, 2019, 7 pages.
International Search Report and Written Opinion received for PCT Patent Application No. PCT/EP2017/077446, dated Feb. 6, 2018, 8 pages.

* cited by examiner

METHOD AND SYSTEM FOR DETERMINING A TRAJECTORY OF AN X-RAY IMAGING SYSTEM

FIELD OF THE INVENTION

The invention relates to a method and a system for determining a trajectory of an X-ray imaging system intended to acquire images of a body region of interest.

BACKGROUND OF THE INVENTION

During computed tomography (CT), an X-ray imaging system moves about a given trajectory (e.g. a simple rotation about an axis or a more complex trajectory) in order to obtain images from different projection angles. A 3D volume of a body region of interest is reconstructed from said images.

Before launching the acquisition of the images, a user (e.g. a surgeon or a radiologist) has to make sure that the body region of interest is correctly positioned relative to said trajectory such that the reconstructed 3D volume contains the region of interest and that the image quality is good.

Thus, in the case of a circular trajectory, the user seeks to position the body region of interest at the center of the trajectory.

To that end, the current procedure for centering the body region of interest comprises at least two steps, which may, in many cases, be iterated several times.

During this method, the patient may be lying on a table at least partially surrounded by the X-ray imaging system.

In a first step, the X-ray imaging system is oriented such that the X-ray beam is vertical, and a first image (frontal view) is acquired.

In a second step, the X-ray imaging system is oriented such that the X-ray beam is horizontal, and a second image (lateral view) is acquired.

The user thus checks on both images whether the body region of interest is in the center of the image.

If so, he can launch the acquisition of the X-ray images intended to reconstruct a 3D volume containing the region of interest.

In the contrary, if the body region of interest is not correctly positioned in at least one of the first and second images, the user has to move the patient relative to the X-ray imaging system (either by moving the table or by moving the X-ray imaging system) and to carry out again the procedure. This increases the X-ray dose to which the patient is subjected. Since said additional irradiation is only used to position the patient relative to the X-ray imaging system and not to image the body region of interest, it should be avoided.

The iteration of the centering procedure mainly results from the fact that while the vertical orientation of the X-ray beam is quite easy to achieve using a positioning laser attached to the X-ray imaging system, the horizontal orientation is much difficult to adjust because the height of the region of interest in the horizontal plane is more difficult to assess even thanks to the use of a laser beam.

Apart from exposing the patient to excessive irradiation, said iterative procedure is time-consuming and burdensome.

It is thus desirable to obtain more easily a suitable trajectory of the X-ray imaging system relative to the body region of interest.

Document US 2015/003577 discloses a method for positioning a body region of interest in the isocenter of a CT imaging system. Such a system comprises a C-arm bearing an X-ray tube and an X-ray detector arranged opposite each other, which is able to rotate about an axis of rotation in order to obtain X-ray images from different projection angles. The isocenter is defined as the point at which the central beam of radiation intersects with the axis of rotation. In this method, a topogram of the patient is acquired by the CT imaging system, said topogram comprising a first section obtained by translating the C-arm along the patient's body while the C-arm is oriented in a first direction and a second section obtained by translating the C-arm along the patient's body while the C-arm is oriented in a second direction perpendicular to the first one. Based on said two sections, a distance between the body region of interest and the isocenter during the recording of the topogram can be determined. Then, either the patient or the imaging system is moved by this distance to bring the body region of interest into the isocenter, and the acquisition of the X-ray images is launched.

However, the acquisition of the topogram still requires exposing the patient to a significant dose of X-rays.

BRIEF DESCRIPTION OF THE INVENTION

A goal of the invention is to provide a method and a system for determining a trajectory of a motorized X-ray imaging system intended to acquire 2D images of a body region of interest of a patient, in view of reconstructing a 3D volume of the region of interest. Another goal of the invention is to provide a method that reduces the time needed to achieve the trajectory of the X-ray imaging system. Another goal of the invention is to optimize the size of the reconstructed 3D volume without increasing the size of the panel detector of the X-ray imaging system.

The invention thus provides a method for determining a trajectory of a motorized X-ray imaging system for acquiring images of a patient to whom a phantom comprising radiopaque fiducials having a known spatial arrangement has been attached so as to be visible on at least one 2D image of a body region of interest acquired by the X-ray imaging system, the method comprising the following steps:
  acquiring one first 2D image of the phantom by the X-ray imaging system in a given position;
  detecting the fiducials of the phantom in said acquired first image;
  based on said detected fiducials, determining the position of the phantom in a referential of the X-ray imaging system;
  determining a set of positions of the X-ray imaging system adapted to acquire a set of 2D X-ray images such that said set of images complies with at least one imposed requirement on the position of the phantom relative to a part of said set of images,
  combining said set of determined positions to determine a trajectory of the X-ray imaging system with respect to the position of the phantom.

A trajectory is defined as a combination of successive positions of the X-ray imaging system. A 2D X-ray image may be acquired in each of said positions and the set of acquired images is used to reconstruct a 3D volume.

According to an embodiment, the imposed requirement varies depending on the position of the X-ray imaging system.

The method may further comprise implementing said determined trajectory to acquire 2D X-ray images and reconstructing a 3D volume of the body region of interest of the patient from said acquired images.

According to an embodiment, the imposed requirement on the position of the phantom is an estimated position of the region of interest relative to the phantom.

According to an embodiment, the method further comprises interactively entering the imposed requirement on the position of the phantom.

According to an embodiment, the trajectory of the X-ray imaging system is determined such that a substantial number of acquired 2D X-ray images contain a substantial portion of the phantom. Advantageously, all acquired 2D X-ray images contain all fiducials of the phantom.

According to an embodiment, the method further comprises a step of displaying instructions to move the X-ray imaging system relative to the phantom to achieve said determined trajectory.

Alternatively, the method may comprise a step of automatically moving the X-ray imaging system relative to the phantom to achieve said determined trajectory.

According to an embodiment, the fiducials of the phantom comprise spheres.

According to an embodiment, the body region of interest comprises a vertebra.

According to an embodiment, the first image of the phantom is a frontal view and one position of the set of positions of the X-ray imaging system is a lateral view.

Alternatively, the first image of the phantom may be a lateral view and one position of the set of positions of the X-ray imaging system is a frontal view.

Another object of the invention is a system for determining a trajectory of a motorized X-ray imaging system, comprising a processor configured for being coupled to the X-ray imaging system and for:
- obtaining a first 2D image of a phantom comprising radiopaque fiducials having a known spatial arrangement attached to a patient, acquired by the X-ray imaging system in a given position,
- detecting the fiducials of the phantom in said acquired first image;
- based on said detected fiducials, determining the position of the phantom in a referential of the X-ray imaging system;
- determining a set of positions of the X-ray imaging system adapted to acquire a set of 2D X-ray images of the region of interest such that said set of 2D X-ray images complies with at least one imposed requirement on the position of the phantom relative to a part of said set of images,
- combining said set of determined positions to determine a trajectory of the X-ray imaging system with respect to the position of the phantom.

The system may further comprise a motorized X-ray imaging system coupled to the processor.

BRIEF DESCRIPTION OF THE DRAWINGS

Further features and advantages of the invention will be apparent from the description that follows, based on the appended drawings, wherein.

DETAILED DESCRIPTION OF EMBODIMENTS OF THE INVENTION

Figure 1:
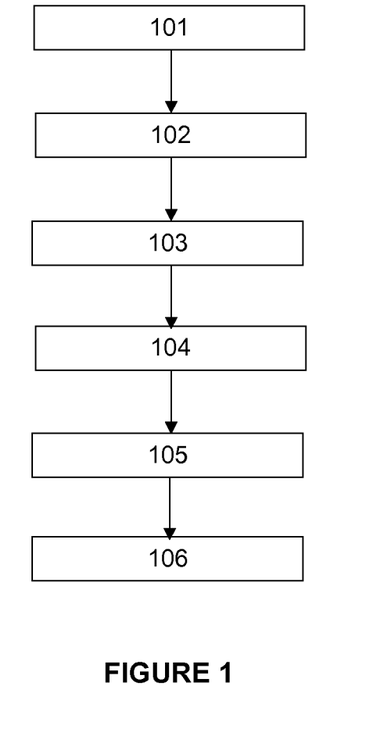
FIG. 1 shows a flowchart of the method.

FIG. 1 is a flowchart presenting the main steps of the method.

Said method is implemented using a system comprising a computer coupled to a motorized X-ray imaging system.

The computer comprises at least one processor configured to implement an algorithm allowing executing at least part of the method steps. The computer may also comprise a memory wherein various parameters of the method can be stored. The computer may further comprise a display for displaying information to a user.

The system further comprises an X-ray imaging system, e.g. a C-arm, intended to acquire a plurality of 2D images in order to reconstruct a 3D volume of a region of interest. The X-ray imaging system comprises an X-ray source and a panel detector located opposite the X-ray source.

The X-ray imaging system is motorized on at least one movement which contributes to generate a 3D acquisition trajectory, i.e. each movement of the system according to a degree of freedom is generated by a respective motor.

Each motor is associated to an encoder allowing knowing, at any time, the relative position of the X-ray imaging system with respect to a reference position. When a 2D image is acquired, the corresponding position of the imaging system is recorded. Thus, each 2D image is recorded in the referential of the imaging system.

According to an embodiment, the X-ray imaging system comprises three motorized degrees of freedom: one translation along X-axis (transversal to the patient's body who is lying on a table), one translation along Z-axis (vertical direction) and one orbital rotation around Y-axis (longitudinal axis). Said movements may be combined to generate a complex trajectory of the X-ray imaging system. Of course, the X-ray imaging system may comprise additional motorized degrees of freedom, which can also be involved in the generation of a complex trajectory.

Advantageously, the computer is coupled to the X-ray imaging system such that, when the trajectory of the X-ray imaging system has been determined, the processor controls the motors of the X-ray imaging system to achieve said determined trajectory.

In a preliminary step that does not belong to the claimed method, a phantom comprising radiopaque fiducials is attached to the patient.

The radiopaque fiducials have a determined spatial arrangement, which may be known, for example, by metrology or based on the assumption that the manufacturing process of the phantom is precise and reproducible enough to ensure that the desired position of the fiducials is obtained.

Advantageously, the geometry of the phantom and the arrangement of the radiopaque fiducials are specific to the region of interest to be imaged.

The phantom is attached to the patient so as to be visible on at least one image acquired by the X-ray imaging system.

Various attachment means may be used, provided that the phantom remains in a fixed position relative to the region of interest during acquisition of the images. In an embodiment, the phantom may be attached directly to a bone of the region of interest. In another embodiment, the phantom may be attached to the patient's skin (e.g. by an adhesive) in the vicinity of the region of interest. According to an embodiment, the phantom is attached to the patient by a non-invasive method, without involving any surgical step.

At least one requirement regarding the position of the phantom relative to at least part of the images acquired to reconstruct a 3D volume of the region of interest is imposed by the system (for example, the requirement may have been defined previously for a specific medical application) and/or by a user. Said at least one requirement is selected so as to ensure that the reconstruction of the 3D volume is optimal according to at least one axis of reconstruction.

For example, said requirement may be based on the following criterion: a substantial portion of the phantom (i.e. a substantial number of the fiducials) is visible on a substantial part of the 2D X-ray images, preferably on all the 2D X-ray images. Indeed, the more fiducials are visible on the 2D X-ray image, the better the quality of the reconstruction of the 3D volume. In particular, it is considered that a minimum threshold for the number of fiducials and the number of 2D X-ray images where fiducials are visible is 50%; a reasonable threshold is 80%, the optimum being 100%.

In another example, said requirement may be based on the following criterion: the phantom is tangent to a side of at least part the 2D X-ray images.

Of course, other criteria could be used without departing from the scope of the invention.

Said requirement may be represented by an estimated distance between the phantom and the region of interest. For example, in an application to spine surgery, where the patient is lying in prone position and the phantom is placed above the patient's skin, it is generally assumed that the distance between the phantom and the vertebra—which is the region of interest to be imaged—is of about 10 cm.

Said requirement may also be based on an a priori knowledge of the region of interest and of the acquisition views that bring relevant information to a user. For example, in the case of spine, the user generally focuses on the vertical extent of the vertebra. In such case, lateral images are of greater interest than frontal images. In another example, in the case of an elongated bone, the user may focus on the longitudinal extent of the bone. In such case, frontal images may be of greater interest than lateral images.

According to an embodiment, the requirement is determined prior to implementation of the method and is stored in a memory of the computer readable by the processor, or loaded by the processor in view of carrying out the method. For example, the requirement may be a standard distance between the phantom and the region of interest.

According to another embodiment, the requirement is entered interactively by a user. To that end, the computer may comprise a display coupled to the processor and configured to display a user interface through which the user may enter a specific requirement. For example, the requirement may depend on the size and/or weight of the patient, and the user may thus input a requirement adapted to said size and/or weight. For example, for a patient suffering from obesity, the distance between the phantom and the vertebra may be of about 12 cm instead of 10 cm.

In a first step 101, a single first image of the patient is acquired. This image is the only one used to determine a set of positions of the X-ray imaging system—different from the first position—adapted to acquire a set of 2D X-ray image images, based on said position of the phantom and on the at least one imposed requirement of the position of the phantom within said second image.

According to an embodiment, the X-ray imaging system may be placed in a frontal position to acquire said first image, such that the X-ray beam is oriented vertically and passes through the phantom. The user can control this vertical orientation using a positioning laser which is currently used for this purpose.

However, this first position of the X-ray is not limitative and the user could select any other position of the X-ray to acquire the first image without departing from the scope of the present invention, provided that he makes sure that the phantom will be visible on said image.

In step 102, the radiopaque fiducials of the phantom are detected on the image acquired in step 101.

Figure 2:
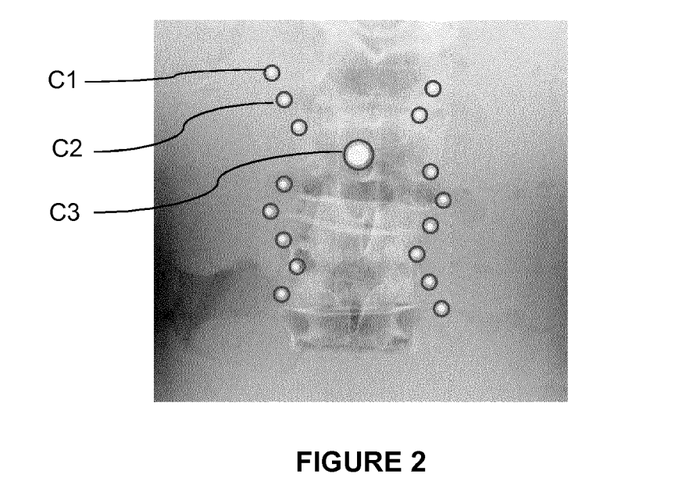
FIG. 2 shows an X-ray frontal image of a patient's spine, with radiopaque fiducials of the phantom visible on the image.

FIG. 2 shows an X-ray frontal image of a patient's spine acquired with the X-ray beam oriented vertically, with radiopaque fiducials of the phantom visible on the image. The detection of the fiducials may be based on pattern detection algorithms that are known to the skilled person and will thus not be described in detail in the present text.

In this non-limitative embodiment, the radiopaque fiducials are spheres.

Figure 3:
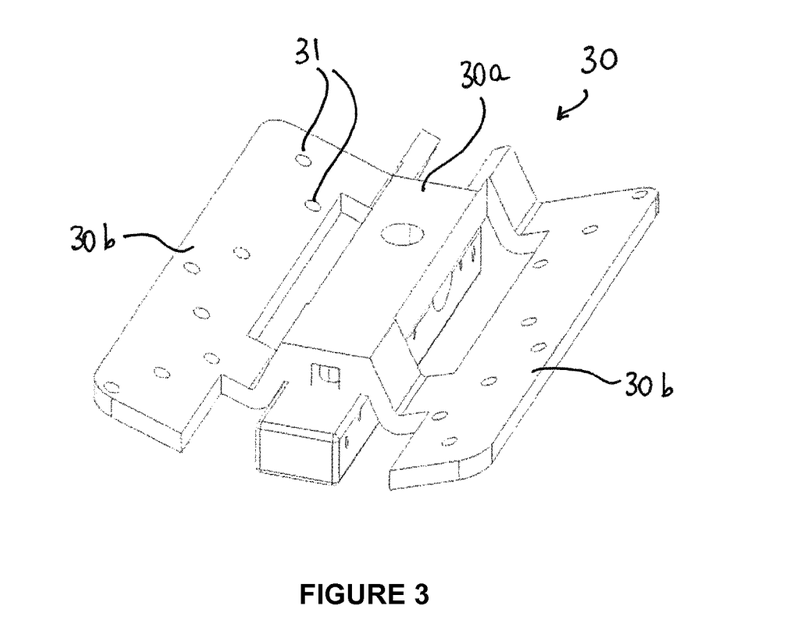
FIG. 3 shows an embodiment of a phantom comprising radiopaque fiducials seen in the image of FIG. 2.

Once the fiducials have been detected as 2D circles C1, C2, C3, etc., the center of each circle is associated with the center of each sphere of the phantom, which is shown in FIG. 3. In the illustrated embodiment, the phantom 30 comprises a central portion that is intended to be fixed to the patient and two lateral wings 30b extending on either side of said central portion 30a. Radiopaque fiducials 31 are embedded in the central portion and the lateral wings with a known geometry. Preferably, the lateral wings are integral with the central portion. Depending on the application, the base and lateral wings may substantially extend in a plane; otherwise, the lateral wings may be inclined with respect to the central portion. In another embodiment, the wings may extend above the central portion. Of course, this design of the phantom is not limitative.

Figure 4:
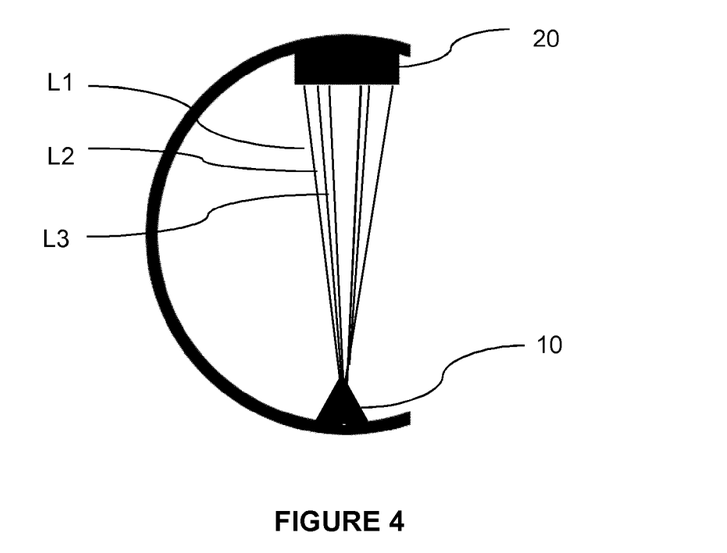
FIG. 4 schematically illustrates the computation of lines corresponding to the back-projection of the centers of the circles representing the radiopaque fiducials.

In step 103, lines L1, L2, L3, etc. corresponding to the back-projection of the centers of the respective circles C1, C2, C3, etc., which extend from the X-ray source 10 to the panel detector 20, are computed based on the geometric calibration of the X-ray imaging system (see FIG. 4).

Figure 5:
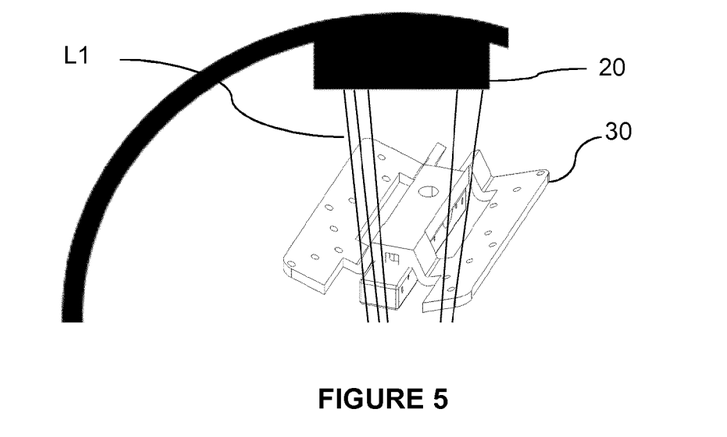
FIG. 5 schematically illustrates the registration of the phantom with the lines computed in FIG. 4.

In step 104, the phantom 30 is registered with the lines L1, etc. computed in step 103 (see FIG. 5).

In step 105, the at least one above-mentioned imposed requirement is taken into account to determine a set of positions of the X-ray imaging system adapted to acquire a set of images such that the imposed requirement is met.

Figure 6:
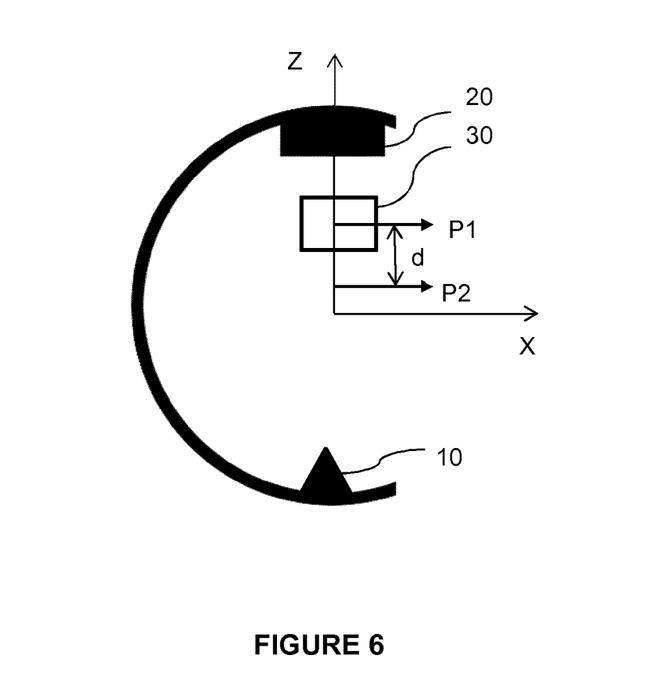
FIG. 6 schematically illustrates the computation of a position of the X-ray imaging system different from the position of the X-ray imaging system in FIG. 2.

For example, in the case illustrated in FIG. 6, the current position P1 of the phantom 30 is located at a given distance d in the vertical (Z) direction from an optimal position P2 of the phantom. In such case, the processor can control the motor(s) of the X-ray imaging system so as to provide a translation along the vertical axis by said distance d. It is to be noted that the displacement of the X-ray imaging system and of the phantom is relative, meaning that the X-ray imaging system and/or the phantom (e.g. by moving a table on which the patient is lying) can be moved to obtain said second position.

According to an embodiment, in step 106, the X-ray imaging system is then moved to each position of the determined set of positions. This displacement may be made automatically or manually. In the latter case, an information about the desired relative position of the X-ray imaging system and the phantom may be displayed to the user. For example, a distance according to a given axis can be provided to the user to move the table on which the patient is lying and/or move the X-ray imaging system in order to reach the desired relative position.

Among this set of positions defining the trajectory of the X-ray imaging system, one position (hereinafter called second position) may be used to check whether the second position effectively complies with the imposed requirement(s). For example, if the first position was a frontal position, the second position may be a lateral view, and conversely. An image may be acquired by the X-ray imaging system in this second position and the user may see whether, for example, the phantom is in the intended position within the image and/or the region of interest is entirely in the image.

Figure 7:
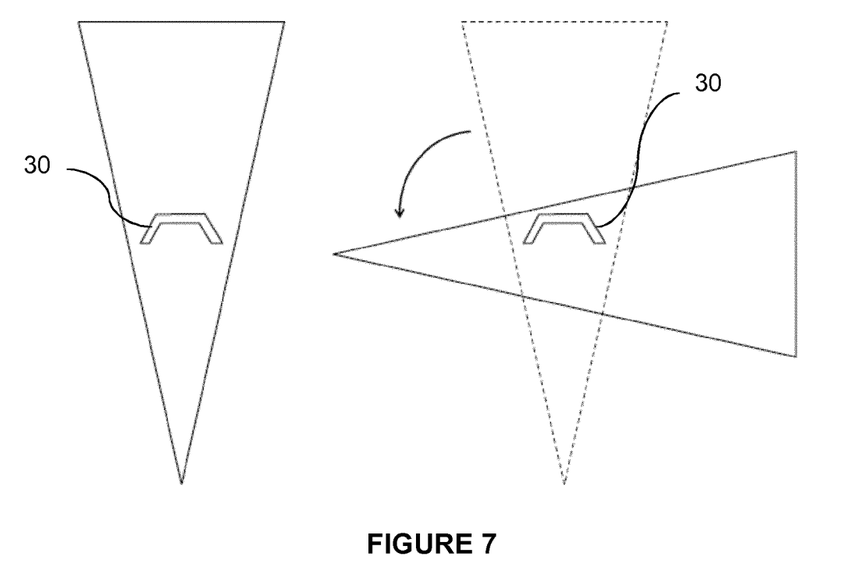
FIG. 7 shows schematically the X-ray beam in a first (frontal) position of the X-ray imaging system (left) and in a second (lateral) position of the X-ray imaging system with the phantom tangent to the X-ray beam (right)

For example, FIG. 7 shows schematically the X-ray beam in a first (frontal) position of the X-ray imaging system (left) and in a second (lateral) position of the X-ray imaging system with the phantom 30 visible in the X-ray image, tangent to the X-ray beam (right).

Figure 8:
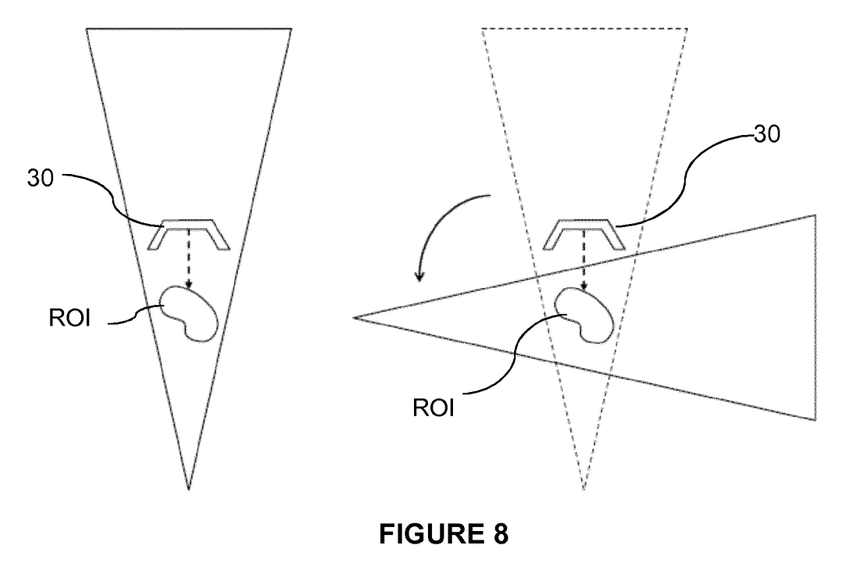
FIG. 8 shows schematically the X-ray beam in a first (frontal) position of the X-ray imaging system (left) and in a second (lateral) position of the X-ray imaging system in which the region of interest is entirely comprised in the beam (right).

According to another embodiment, FIG. 8 shows schematically the X-ray beam in a first (frontal) position of the X-ray imaging system (left) and in a second (lateral) position of the X-ray imaging system in which the region of interest ROI is entirely comprised in the beam (right). In such case, the phantom 30 may not be visible on the X-ray image.

This step of determination of the second position can be considered as a "centering" step, since it allows determining a suitable positioning of the X-ray imaging system for acquiring a good image of the region of interest. It can also be considered as a starting or final point for the trajectory to be computed (although this second position may in fact be any position of the trajectory).

As explained above, the centering method described above requires only one image. The iterations to position correctly the X-ray imaging system relative to the region of interest are thus removed. In addition, the patient is less exposed to useless radiation.

As noted above, the trajectory of the X-ray imaging system is determined by combining a set of positions of the X-ray system taking into account the imposed requirement(s). Thus, the trajectory is constituted by a set of positions determined by more than one movement, i.e. a combination of translations and rotations for at least some positions of the set (complex trajectory). In such a complex trajectory, the distance between the patient and the panel detector varies. In particular, for the views that are most relevant to the user, the panel detector may be brought closer to the patient in order to maximize the size of the region of interest in the 2D X-ray image.

The imposed requirement(s) may vary depending on the position of the X-ray imaging system. There may even not be any imposed requirement for the some of the positions of the X-ray imaging system, these positions thus being determined only by an orbital movement. For example, the imposed requirement(s) may be applied for the views that are most relevant to the user, and not applied for the views that are less relevant to the user. For example, still referring to the spine surgery application, one may seek a greater size of the reconstructed 3D volume by imposing a requirement on the position of the phantom relative to the images for lateral views, and not for frontal views.

An advantage of a complex trajectory—as compared to an isocentric trajectory which consists of an orbital movement—is that the 3D reconstructed volume may be maximized in at least one selected direction. Besides, the dose of radiation received by the patient is all the more reduced that the panel detector is close to the patient.

Although most examples have been given in the case of spine surgery, it is to be noted that the invention is not limited to this surgical application, but is also applicable to other medical fields.

REFERENCES

US 2015/003577

The invention claimed is:
1. A method for determining a trajectory of a motorized X-ray imaging system for acquiring images of a patient to whom a phantom comprising radiopaque fiducials having a known spatial arrangement has been attached so as to be visible on at least one 2D image of a body region of interest acquired by the X-ray imaging system, the method comprising the following steps:
   acquiring one first 2D image of the phantom by the X-ray imaging system in a given position;
   detecting the fiducials of the phantom in said acquired first 2D image;
   based on said detected fiducials, determining the position of the phantom in a referential of the X-ray imaging system;
   determining a set of positions of the X-ray imaging system configured to acquire a set of 2D X-ray images of the region of interest such that said set of 2D X-ray images complies with at least one imposed requirement on the position of the phantom relative to a part of said set of 2D X-ray images,
      combining said set of determined positions to determine a trajectory of the X-ray imaging system with respect to the position of the phantom.
2. The method according to claim 1, wherein the imposed requirement varies depending on the position of the X-ray imaging system.
3. The method according to claim 1, further comprising implementing said determined trajectory to acquire 2D X-ray images and reconstructing a 3D volume of the body region of interest of the patient from said acquired 2D X-ray images.
4. The method according to claim 1, wherein the imposed requirement on the position of the phantom is an estimated position of the region of interest relative to the phantom.
5. The method according to claim 1, further comprising interactively entering the imposed requirement on the position of the phantom.
6. The method according to claim 1, wherein the trajectory of the X-ray imaging system is determined such that a substantial number of acquired 2D X-ray images contain a substantial portion of the phantom.
7. The method according to claim 6, wherein all acquired 2D X-ray images contain all fiducials of the phantom.
8. The method according to claim 1, further comprising a step of displaying instructions to move the X-ray imaging system relative to the phantom to achieve said determined trajectory.

9. The method according to claim 1, further comprising a step of automatically moving the X-ray imaging system relative to the phantom to achieve said determined trajectory.

10. The method according to claim 1, wherein the fiducials of the phantom comprise spheres.

11. The method according to claim 1, wherein the body region of interest comprises a vertebra.

12. The method according to claim 1, wherein the first image of the phantom is a frontal view and wherein one position of the set of positions of the X-ray imaging system is a lateral view.

13. The method according to claim 1, wherein the first image of the phantom is a lateral view and wherein one position of the set of positions of the X-ray imaging system is a frontal view.

14. A system for determining a trajectory of a motorized X-ray imaging system, comprising a processor configured for being coupled to the X-ray imaging system and for:

obtaining a first 2D image of a phantom comprising radiopaque fiducials having a known spatial arrangement attached to a patient, acquired by the X-ray imaging system in a given position, detecting the fiducials of the phantom in said acquired first 2D image;

based on said detected fiducials, determining the position of the phantom in a referential of the X-ray imaging system;

determining a set of positions of the X-ray imaging system configured to acquire a set of 2D X-ray images of the region of interest such that said set of 2D X-ray images complies with at least one imposed requirement on the position of the phantom relative to a part of said set of 2D X-ray images, combining said set of determined positions to determine a trajectory of the X-ray imaging system with respect to the position of the phantom.

15. The system according to claim 14, further comprising a motorized X-ray imaging system coupled to the processor.

\* \* \* \* \*